United States Patent [19]

Lunnen et al.

[11] Patent Number: 5,053,330
[45] Date of Patent: Oct. 1, 1991

[54] METHOD FOR PRODUCING THE MWOI RESTRICTION ENDONUCLEASE AND METHYLASE

[75] Inventors: Keith D. Lunnen, Newbury; Geoffrey G. Wilson, Boxford, both of Mass.

[73] Assignee: New England Biolabs, Inc., Beverly, Mass.

[21] Appl. No.: 332,685

[22] Filed: Mar. 13, 1989

[51] Int. Cl.⁵ .................... C12N 15/52; C12N 9/22; C12N 1/21

[52] U.S. Cl. .................... 435/172.3; 435/199; 435/252.33; 435/320.1; 536/27; 935/29; 935/73; 935/80

[58] Field of Search ............ 435/172.3, 199, 320, 435/252.3; 935/29, 73, 70, 82; 536/27

[56] References Cited

FOREIGN PATENT DOCUMENTS 0193413 3/1986 European Pat. Off. .

OTHER PUBLICATIONS

Greene, P. J. et al. (1981) J. Biol. Chem., 256(5), 2143-2153.
Newman, A. K. et al. (1981) J. Biol. Chem., 256(5), 2131-2139.
Schoner, B. et al. (1983) Gene, 24, 227-236.
Walber, R. Y. et al. (1984) J. Biol. Chem., 259(12), 8015-8026.
Bickle, T. A. et al. (1980), Gene, 9, 205-212.
Lunnen, K. D. et al. (1989) Gene, 77, 11-19.
Wilson, G. C. (1988) Trends in Generics , 4(11), 314-318.
Lunnen, K. D. et al. (1988) Gene, 74, 25-32.
Borck, K. et al. (1976) Mol. Gen. Genetic, 146, 199-207.
Davis, R. O. et al. (1980) Microbiology, Third Ed., Harper and Row, Pubs., p. 30.
Kosykh et al., Molec. Gen. Genet 178: 717-719, 1980.
Mann et al., Gene 3: 97-112, 1978.
Walder et al., Proc. Natl Acad. Sci. 78: 1503-1507, 1981.
Bouqueleret et al., Nucl. Acid. Res. 12: 3659-3676, 1984.
Gingeras & Brooks, Proc. Natl. Acad. Aci. USA 80: 402-406, 1983.
Theriault & Roy, Gene 19: 355-359, 1982.
Blumenthal et al., J. Bacteriol. 164: 501-509, 1985.
Kiss et al., Nucl. Acid. Res. 13: 6403-6421, 1985.
Szomolanyi et al., Gene 10: 219-225, 1980.
Janulaitis et al., Gene 20: 197-204, 1982.
Kiss & Baldauf, Gene 21: 111-119, 1983.
Walder et al., J. Biol. Chem. 258: 1235-1242, 1983.
Raleigh & Wilson, Proc. Natl. Acad. Sci., USA 83: 9070-9074, 1986.
Winter et al., Syst. Appl. Microbiol. 5: 457-466, 1984.
Konig et al., Arch. Microbiol. 141: 177-180, 1985.
Keiner et al., J. Bacteriol. 169: 1010-1016, 1987.
Schonheit et al., Arch. Microbiol. 127: 59-65, 1980.
Birnboin & Doly, Nucleic Acids Res. 7: 1513, 1979.

*Primary Examiner*—Elizabeth C. Weimar
*Assistant Examiner*—Charles L. Patterson
*Attorney, Agent, or Firm*—Gregory D. Williams; David G. Conlin

[57] ABSTRACT

The present invention is directed to a method for cloning and producing the MwoI restriction endonuclease by 1) introducing the restriction endonuclease gene from M. wolfei into a host whereby the restriction gene is expressed; 2) fermenting the host which contains the plasmid encoding and expressing the MwoI restriction endonuclease activity, and 3) purifying the MwoI restriction endonuclease from the fermented host which contains the plasmid encoding and expressing the MwoI restriction endonuclease activity.

16 Claims, 3 Drawing Sheets

Restriction Endonuclease Assay
Mwo I

METHOD FOR PRODUCING THE MWOI RESTRICTION ENDONUCLEASE AND METHYLASE

BACKGROUND OF THE INVENTION

The present invention relates to clones for the MwoI restriction endonuclease and modification methylase, and the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria tend to possess at most only a small number restriction endonucleases per species. The endonucleases typically are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT),PuGCGCPy and GGCC respectively. *Escherichia coli* RY13, on the other hand, synthesizes only one enzyme, EcoRI, which recognizes the sequence GAATTC While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The breakup that takes place disables many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (EcoRII: Kosykh et al., Molec gen. Genet 178 717-719, (1980); HhaII: Mann et al., Gene 3: 97-112, (1978); PstI: Walder et al., Proc. Nat. Acad. Sci. 78 1503-1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival Another cloning approach involves transferring systems initially characterized as plasmid-borne into *E. coli* cloning plasmids (EcoRV: Bougueleret et al., Nucl. Acid. Res. 12: 3659-3676, (1984); PaeR7: Gingeras and Brooks, Proc. Natl. Acad. Sci. USA 80: 402-406, (1983); Theriault and Roy, Gene 19: 355-359, (1.982); PvuII: Blumenthal et al., J. Bacteriol. 164: 501-509, (1985)).

A third approach, and one that is being used to clone a growing number of systems, involves selecting for an active methylase gene referring to our EPO publication No.: 193413 (BsuRI: Kiss et al., Nucl. Acid. Res. 13: 6403-6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., Gene 10: 219-225, (1980); BcnI: Janulaitis et al, Gene 20: 197-204, (1982); BsuRI: Kiss and Baldauf, Gene 21: 111-119, (1983); and MspI: Walder et al., J. Biol. Chem. 258: 1235-1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning systems in *E. coli* was discovered in the process of cloning diverse methylase genes. Many *E. coli* strains (including those normally used in cloning) have systems that resist the introduction of DNA containing methylated cytosines. (*Raleigh and Wilson, Proc. Natl. Acad. Sci., U.S.A.* 83: 9070–9074, 1986). It is extremely difficult to clone cytosine-specific methylase genes, either alone, or together with their corresponding endonuclease gene, into these strains of *E. coli*. In order to clone these genes, therefore, it is necessary to use mutant strains of *E. coli* in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the MwoI restriction endonuclease and modification methylase derived from *Methanobacterium wolfei* (Winter et al., Syst Appl. Microbiol. 5: 457–466, 1984) as well as related methods for the production of the enzymes. More specifically, this invention relates to clones which express the restriction endonuclease MwoI, an enzyme which recognizes the DNA sequence $GC(N_7)GC$ and cleaves between $N_5$ and $N_6$. MwoI restriction endonuclease produced in accordance with the present invention is substantially pure and free of the contaminants normally found in MwoI preparations made by conventional techniques.

The preferred method for cloning the genes for the MwoI enzymes comprises forming a library containing the DNA from *M. wolfei*, isolating those clones which contain DNA coding for the MwoI modification methylase and screening among these to identify those that also contain the MwoI restriction endonuclease gene.

DETAILED DESCRIPTION OF THE DRAWINGS

The present invention relates to clones of the MwoI restriction and modification genes, as well to the restriction endonuclease MwoI produced from such clones. The MwoI genes are cloned by a method which takes advantage of the fact that certain clones which are selected on the basis of containing and expressing the MwoI modification methylase gene also contain the MwoI restriction gene. The DNA of such clones is resistant to digestion, in vitro, by the MwoI restriction endonuclease. This resistance to digestion affords a means for selectively isolating clones encoding the MwoI methylase and restriction endonuclease.

Figure 1:
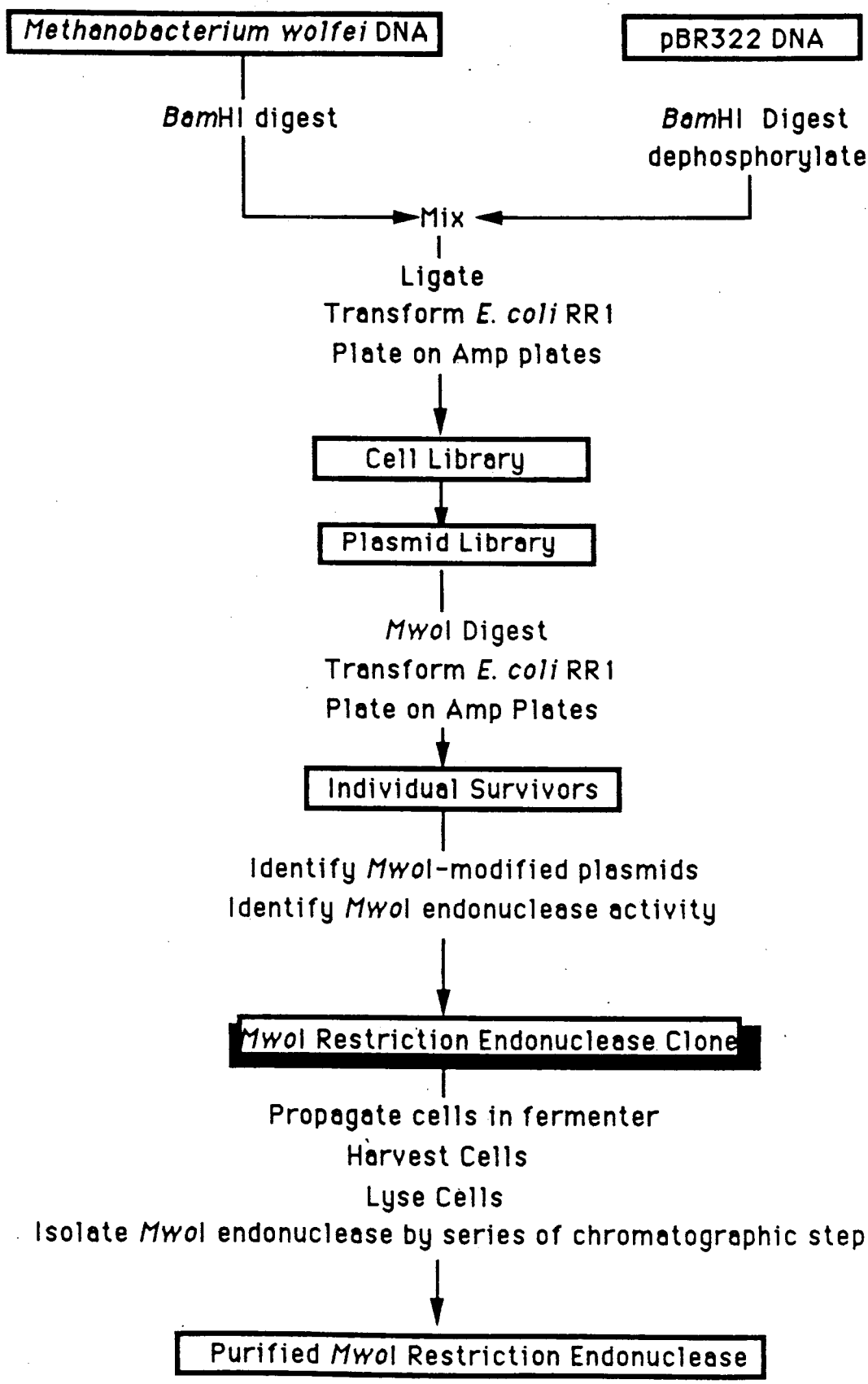
FIG. 1 illustrates the scheme for cloning and producing the MwoI restriction endonuclease.

The method described herein by which the MwoI restriction gene and methylase gene are preferably cloned and expressed are illustrated in FIG. 1, and they include the following steps:

1. The growth and lysis of *Methanobacterium wolfei*. *M. wolfei* has been described in the publication Winter et al., Syst. Appl. Microbiol. 5: 457–466, (1984). Cultures of *M. wolfei* (DSM2970) are deposited at Deutsche Sammlung von Mikoorganismen, Grisebachstrasse 8, D-3400 Gottingen, Federal Republic of Germany. Samples of this bacterium are also available from Dr. John N. Reeve, Dept. of Microbiology, The Ohio State University, 484 W. 12th Street, Columbus, OH 43210 (USA).

2. The DNA of *M. wolfei* is purified.

3. The DNA is digested partially with the restriction endonuclease BamHI, HindIII and PstI.

4. The digested DNA is ligated to a cloning vector, such as a pBR322 derivative containing a BamHI, HindIII or PstI site. The resulting mixture is used to transform an appropriate host such as *E coli* strain RR1 (ATCC 31343).

5. The DNA/cell mixture is plated on antibiotic media selective for transformed cells, such as ampicillin. After incubation, the transformed cell colonies are collected together into a single culture, the primary cell library.

6. The recombinant plasmids are purified in toto from the primary cell library to make a primary plasmid library.

7. The plasmid library is then digested to completion in vitro with the MwoI restriction endonuclease, which was prepared from autolysed *M. wolfei* cells (Konig et al., 1985; Kiener et al., 1987). The MwoI restriction endonuclease activity is purified by standard protein purification techniques such as affinity-chromatography, and ion-exchange chromatography. MwoI restriction endonuclease digestion causes the selective destruction of unmodified, non-methylase-containing, clones, resulting in an increase in the relative frequency of MwoI methylase-carrying clones.

8. The digested plasmid library DNA is transformed back into an appropriate host, such as *E. coli* strain RR1, and transformed colonies are again obtained by plating on antibiotic plates. The colonies are picked and their DNA is analyzed for the presence of the MwoI modification gene in the following manner: The plasmid DNA that they carry is purified and incubated vitro with MwoI restriction endonuclease to determine whether it is resistant to digestion by MwoI. The total cellular DNA (chromosomal and plasmid) of the clone is also purified and incubated with MwoI restriction endonuclease. The DNA of clones that carry the MwoI methylase gene should be modified, and both the plasmid DNA and the total DNA should be found to be substantially, or completely resistant to digestion.

9. Clones carrying the MwoI restriction endonuclease are identified by preparing crude extracts of those clones identified in step 8 as carrying the MwoI methylase gene, and assaying the extracts for MwoI restriction endonuclease activity.

10. The MwoI restriction endonuclease may be produced from clones carrying the MwoI restriction and modification genes by propagation in a fermenter in a rich medium containing ampicillin. The cells are thereafter harvested by centrifugation and disrupted by sonication to produce a crude cell extract containing the MwoI restriction endonuclease activity.

11. The crude cell extract containing the MwoI restriction endonuclease activity is purified by standard protein purification techniques such as affinity-chromatography, and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of MwoI Restriction Endonuclease Gene

1. Growth and lysis of *M. wolfei*: *M. wolfei* cultures were grown in 20L of the minimal medium described by Schonheit et al., Arch. Microbiol. 127: 59–65, (1980), in a 24L New Brunswick anaerobic fermentor at 62° C. The medium was reduced by addition of 0.5g $Na_2S.9H_2O$/L and 0.5g L-Cysteine.HCl/L. *M. wolfei* requires tungsten for growth (Winter et al., 1984) and so the trace elements solution was supplemented with 264 mg $Na_2WO_4.2H_2O$/L. The medium was sparged by bubbling with an 80% $H_2$:20% $CO_2$ mixture during fermentation. Smaller cultures (20 ml) were grown in 100 ml stoppered serum flasks pressurized to 300Kpa with the $H_2$:$CO_2$ gas mixture. Lysates of *M. wolfei* were obtained by autolysis (Konig et al., Arch. Microbiol. 141: 177–180, (1985); Kiener et al., *J. Bacteriol.* 169: 1010–1016, (1987)). 70 gm wet weight of cells were harvested during exponential growth, resuspended in 600 ml of minimal medium, and then incubated without agitation at 62° C. in a serum flask under an atmosphere of 80% $N_2$:20% $CO_2$. Starvation for $H_2$ resulted in complete lysis after approximately 48 h. The autolysate was stored at −70° C.

2. Purification of DNA: 5 ml of thawed autolysate was mixed with 5 ml of 10 mM Tris.HCl, pH 7.4, 10 mM EDTA, 0.25 M sucrose, 20 μg proteinase K/ml. Sodium dodecyl sulfate was added to 1% W/V and the solution was incubated at 60° C. for 30 min. 0.5 ml 5M NaCl was added and the tube was placed on ice for 2h. The solution was cleared by centrifugation at 17,000g for 15 min then the nucleic acids were precipitated by the addition of an equal volume of isopropanol. The precipitate was dissolved in 2 ml of TE buffer (10mM Tris.HCl pH 8.0, 1 mM EDTA), then extracted with phenol and chloroform. The nucleic acids were again precipitated, by addition of 200 μl 7.5M ammonium acetate and 2.5 volumes of 95% ethanol. The precipitate was washed with 70% ethanol, dried, and then redissolved in TE buffer containing 1 μg RNase/ml.

3. Digestion of DNA The purified DNA was cleaved partially with BamHI. DNA was diluted to a concentration of 100 micrograms per ml in 50mM Tris pH 7.5, 100mM NaCl, 10mM $MgCl_2$, 10mM 2-mercaptoethanol, and 0.5 units of BamHI per microgram of DNA was added to a first tube and then transferred to a second tube to achieve 0.25 units BamHI/μg and so on, each succeeding tube receiving half of the previous amount of BamHI. The DNA was digested for one hour at 37° C., then the digestions were terminated by heating to 72° C. for 10 minutes. Tubes exhibiting moderate, but incomplete digestion were chosen as the source of partial digest fragments for cloning. (These were the 0.5 u/μg, 0.25 u/μg and 0.1 u/μg tubes. The three solutions were mixed together and used as described below.)

4. Ligation: The digested DNA was ligated to pBR322 as follows: 2.0 μg of BamHI-digested *M. wolfei* DNA (40 μl) was mixed with 1.0 μg of BamHI-cleaved and dephosphorylated pBR322 (10 μl). 20 μl of 10X ligation mix (500mM Tris, pH 7.5, 100mM MgCl2, 100mM DTT, 5mM ATP) was added, plus 130 μl of sterile distilled water to bring the final volume to 200 μl. 7.5 μl of T4 DNA ligase was added and the mixture was incubated at 17° C. for 4 hours, then sterilized by the addition of 10 μl of chloroform. Approximately 125 μl of the ligated DNA was used to transform *E. coli* strain RR1 as follows: The DNA was mixed with 1.0 ml of SSC/$CaCl_2$ (50mM NaCl, 5mM $Na_3$ Citrate, 67mM $CaCl_2$) on ice and 2.0 ml of ice-cold competent *E. coli* RR1 (hsd R−M−, ATCC No. 31343) cells were added. After a 5-minute incubation at 420° C., the cells were diluted by the addition of 8 ml of Luria-broth (L-broth) then incubated at 37° C. for 4 hours.

5. Primary Cell Library: The transformed cell culture was briefly centrifuged, the supernatant was discarded and the cells were resuspended in 1.0 ml of L-broth. 200 μl portions were plated onto Luria-agar (L-agar) plates containing 100 μg/ml ampicillin. After overnight incubation at 37° C., the plates were each flooded with 2.5 ml of 10 mM Tris, pH 7.5, 10mM $MgCl_2$ and the transformed colonies were scraped together and pooled to form the primary cell library.

6. Primary Plasmid Library: The primary plasmid library was prepared as follows 2.5 ml of the primary cell library was inoculated into 500 ml of L-broth containing 100 μg/ml ampicillin. The culture was shaken overnight at 37° C. then centrifuged at 4000 rpm for 5 minutes. The supernatant was discarded and the cell pellet was resuspended in 10 ml of 25% sucrose, 50mM Tris, pH 8.0, at room temperature. 5ml of 0.25M EDTA, pH 8.0, was added, followed by 3 ml of 10 mg/ml lysozyme in 0.25M Tris, pH 8.0. The solution was left on ice for 1 hour, then 12 ml of lytic mix (1% Triton X-100, 50mM Tris, pH 8.0, 67mM EDTA) was forcefully pipetted in, and the cell suspension was gently swirled to achieve lysis. After lysis, the mixture was transferred to a 50 ml plastic centrifuge tube and spun at 17000 rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10mM Tris, pH 8.0, 1 mM EDTA, 100mM NaCl) was added to the mixture. The solution was transferred to two 5/8 in. × 3 in. polyallomer centrifuge tubes and sealed. These tubes were then spun in a Beckman Ti70 rotor for 42 hours at 44000 rpm, 17° C. To collect the plasmids, the tubes were illuminated with ultraviolet light, the tops were pierced with a scalpel and the lower of the two fluorescent DNA bands was collected by syringe. The lower band from each tube was combined into a screw-top glass tube and the ethidium bromide was removed by extracting four times with an equal volume of water-saturated ice-cold N-Butanol.

The extracted solution was transferred to dialysis tubing and dialyzed for 24 hours against 4 changes of DNA buffer (10mM Tris pH 7.5, 1 mM EDTA). The dialyzed DNA solution was then transferred to a pre-weighed 50 ml sterile centrifuge tube and its volume was measured 5M NaCl was added to a final concentration of 0.4M, then 2 volumes of isopropanol were added and mixed. The solution was stored overnight at −20°

C. to precipitate the DNA. After precipitation, the solution was spun at 15000 rpm, 0° C. for 15 minutes and the supernatant was discarded. The tube was left on the bench to air-dry for 15 minutes, then the DNA pellet was dissolved in 500 μl of DNA buffer and stored at −20° C. The DNA concentration of plasmid libraries prepared in this way was found to be 100 to 200 μg/ml.

7. Digestion of Plasmid Pool: The primary plasmid pool was digested to destroy non-MwoI methylase clones as follows: 2 μg of the plasmid library in 90 μl of MwoI-digestion buffer (10mM Tris.HCl, pH 7.5, 10mM MgCl$_2$, 10mM 2-mercaptoethanol, 150mM NaCl) was incubated with 20 units (3 μl) of partially-purified MwoI restriction enzyme at 65° C. for 1h. The digested DNA was chloroform-extracted and microfuged.

8. Transformation: A 12.5 μl sample from the tube was used to transform 200 μl of competent E. coli RR1. The cell/DNA mixtures were plated onto L-agar plates containing 100 μg/ml ampicillin. After overnight incubation at 37° C., the plates were examined. Digestion of the plasmid library with MwoI was found to have reduced the number of transformants by a factor greater than $10^4$. Individual colonies were picked from the plate and each was inoculated into 10 ml of L-broth containing ampicillin, to prepare a miniculture, and was also streaked onto L-agar plates containing ampicillin to prepare a master stock.

9. Analysis of surviving individuals: Two of the surviving colonies obtained from section 8 were grown up into 10 ml cultures (section 8) and the plasmids that they carried were prepared by the following miniprep purification procedure, adapted from the method of Birnboim and Doly (Nucleic Acids Res. 7: 1513, (1979)).

Miniprep Procedure: Each culture was centrifuged at 8000 rpm for 5 minutes; the supernatant was discarded and the cell pellet was resuspended in 1.0 ml of 25mM Tris, 10mM EDTA, 50mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 μl of 10mM Tris, 1 mM EDTA, pH 8.0. 75μl of 5M NaCl was added to each and the solutions were transferred to Eppendorf tubes containing 575 μl of isopropanol, and again precipitated for 10 minutes at room temperature. The tubes were then spun for 45 seconds in a microfuge, the supernatants were discarded and the pellets were air-dried. The pellets were then dissolved in 500 μl of 10mM Tris, 1 mM EDTA, pH 8.0, containing 100 μg/ml RNase and incubated for 1 hour at 37° C. to digest the RNA. The DNA was precipitated once more by the addition of 50μl of 5M NaCl followed by 350μl of isopropanol. After 10 minutes at room temperature, the DNA was spun down by centrifugation for 45 seconds, the supernatants were discarded and the pellets were redissolved in a final solution of 150μl of 10mM Tris 1mM EDTA, pH 8.0. The plasmid minipreps were subsequently analyzed by digestion with MwoI.

Figure 2:
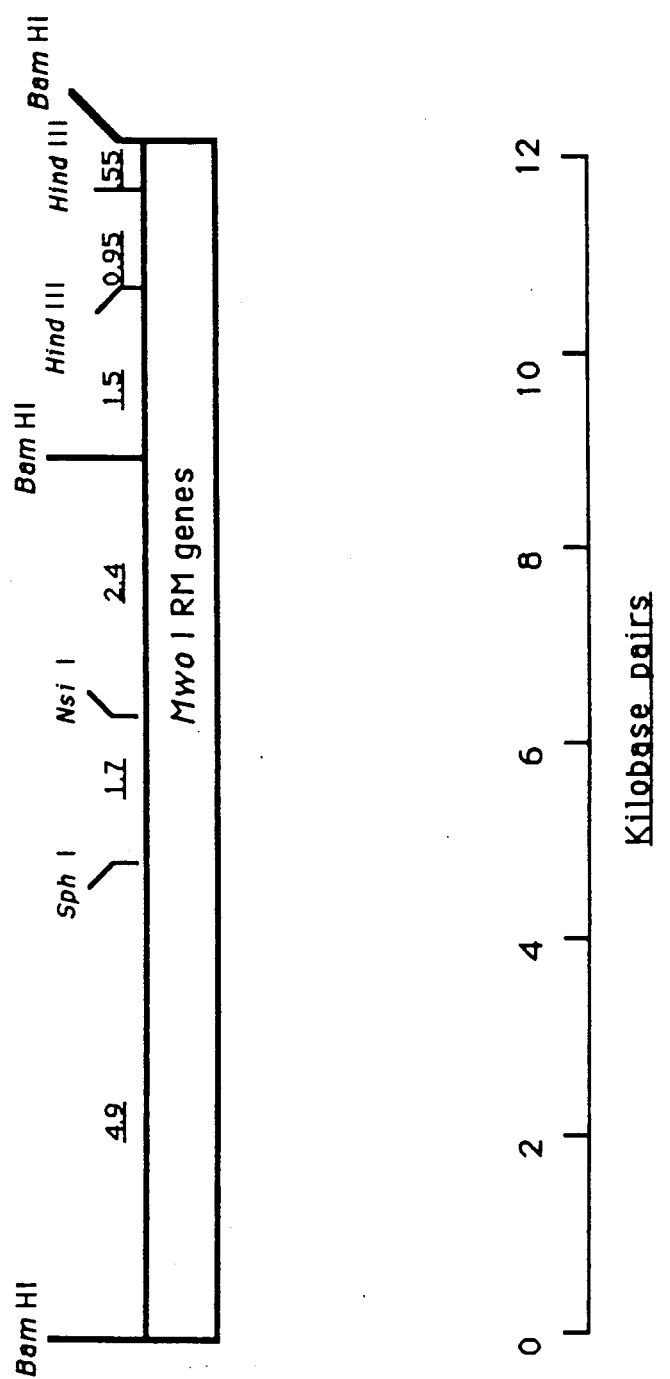
FIG. 2 is a restriction map of a 12 kb BamH I multifragment insert encoding the MwoI restriction endonuclease and modification methylase.

9. MwoI Methylase Gene Clones: Two of the plasmids that were analyzed were found to be substantially, but not fully, resistant to digestion by the MwoI restriction enzyme. The clones carried two BamHI fragments of approximately 9kb and 3kb in length. (See FIG. 2) These plasmids appeared to be identical and were subsequently shown to carry not only the MwoI modification methylase gene but also the MwoI restriction endonuclease gene.

10. MwoI Restriction Gene Clone: pKLMwoIRM 3-1, identified above (section 9) as carrying the MwoI modification methylase gene was also found to carry the MwoI restriction endonuclease gene. This was established by an in vitro restriction endonuclease assay of an extract prepared from E. coli strain ER1398 into which the plasmid had been transferred by transformation.

A sample of pKLMwoIRM 3-1 has been deposited at the American Type Culture Collection under ATCC Accession No. 40874.

Endonuclease Assays: To assay for endonuclease activity, two solutions were prepared:

(i) 10X restriction endonuclease buffer: 100mM Tris, pH 7.5, 100mM MgCl$_2$, 100mM 2-mercaptoethanol, 1500mM NaCl; and (ii) digestion reaction mix: 45 μl HindIII-digested pUC19 (395μg/ml), 35.5 μl 10X restriction endonuclease buffer, 274.5 μl distilled water to achieve 50μg/ml DNA.

Figure 3:
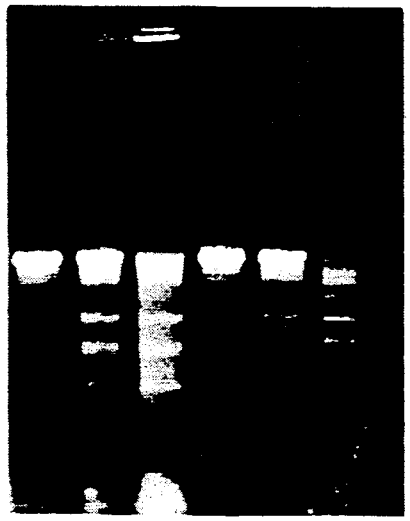
FIG. 3 is a photograph of an agarose gel illustrating MwoI restriction endonuclease activity obtained from the crude extract of pKLMwoIRM 3-1.

The cell extract was prepared as follows: A 50 ml culture of the clone was grown overnight in L-broth plus 100 μg/ml ampicillin at 37° C. and the cells were pelleted by centrifugation at 4000 rpm for 5 minutes. The supernatant was discarded and the pellet was resuspended in 3 ml of sonication buffer (50mM KPO$_4$ pH 7.5, 10mM BME, 0.1mM EDTA). 0.3 ml of sonication buffer containing 10 mg/ml lysozyme was added, the suspension was swirled and then left on ice for 1 hour. A 1 ml sample was transferred to an Eppendorf tube and sonicated gently for three 10-second bursts to disrupt the cells. The tube was spun for 5 minutes in a microfuge and the supernatant was used as the cell extract. To assay the extract, the digestion reaction mix was dispensed into 3 tubes, 150 μl into the first tube and 100 μl into each of the remaining 2 tubes. 7.5 μl of the extract was added to the first tube and mixed 47.5 μl was removed from the first tube and transferred to the second tube, mixed and so on. The first tube thus received 1.0 μl of extract per μg of DNA, the second tube 0.3 μl/μg, the third tube, 0.1 μl/μg and so on. The tubes, each now containing 100 μl, were incubated at 65° C. for one hour, then a 20 μl sample of each was analyzed by gel electrophoresis. The titre of the extract was found to be approximately 50 units per ml, which corresponds to about 1000 units of MwoI restriction endonuclease per gram of cells. (See FIG. 3).

What is claimed is:

1. Isolated DNA coding for the MwoI restriction endonuclease, wherein the isolated DNA is obtainable from the vector pKLMwoIRM3-1.

2. A recombinant DNA vector comprising a vector into which a DNA segment coding for the MwoI endonuclease produced by *Methanobacterium wolfeii* DSM 2970 has been inserted.

3. Isolated DNA coding for the MwoI restriction endonuclease and methylase, wherein the isolated DNA is obtainable from the vector pKLMwoIRM 3-1.

4. A cloning vector which comprises the isolated DNA claim 1.

5. A cloning vector which comprises the isolated DNA of claim 3.

6. The cloning vector of claim 2, wherein the cloning vector comprises pKLMwoIRM 3-1.

7. A host cell transformed by the vector of claim 4, 5 or 6.

8. A method of cloning an MwoI restriction endonuclease gene which comprises:
 (a) forming a library from DNA from wolfei (b) isolating clones which contain the MwoI modification gene; and (c) screening clones containing the modification gene, and isolating clones which contain the MwoI restriction endonuclease gene.

9. The method of claim 8, wherein the library is formed by the steps of:
 (a) purifying DNA from *M. wolfei;*
 (b) digesting the purified DNA to form DNA fragments;
 (c) ligating the fragments into a cloning vector;
 (d) transforming a host cell with the cloning vector of step (c) to form a cell library; and
 (e) purifying recombinant vectors from the cell library to form a plasmid library.

10. The method of claim 9, wherein the cloning vector is pBR322.

11. The method of claim 9, wherein the host cell is a strain of *E. coli* which is hsdR−.

12. The method of claim wherein the clone containing the MwoI modification gene is isolated by digesting the plasmid library with MwoI to form a digestion pool, transforming the digestion pool into a host cell, and selecting clones containing the modification gene.

13. A method for producing MwoI restriction endonuclease comprising:
 (a) purifying DNA from *M. wolfei;*
 (b) digesting the purified DNA with an appropriate restriction endonuclease to form DNA fragments;
 (c) ligating the fragments into the cloning vector to form a DNA mixture;
 (d) transforming a host cell with the DNA mixture of step (c) to form a library;
 (e) isolating clones which contain the MwoI modification methylase gene;
 (f) screening clones containing the MwoI modification methylase gene, and isolating clones which contain the MwoI restriction endonuclease gene;
 (g) culturing the host cells containing the clones of step (f); and
 (h) recovering MwoI restriction endonuclease from the culture.

14. The method of claim 13, wherein the cloning vector is a plasmid or viral DNA molecule.

15. The method of claim 14, wherein the plasmid is pBR322.

16. A method of producing MwoI restriction endonuclease comprising culturing a host cell transformed with the vector of claim 4, 5 or 6 under conditions suitable for the expression of said endonuclease.

* * * * *

UNITED STATES PATENT AND TRADEMARK OFFICE
CERTIFICATE OF CORRECTION

PATENT NO. : 5,053,330
DATED : October 1, 1991
INVENTOR(S) : Keith D. Lunnen, et al.

It is certified that error appears in the above-identified patent and that said Letters Patent is hereby corrected as shown below:

Col. 5, line 54, "DNA" should be --DNA:--. (add a space after DNA:)

Col. 6, line 15, "420°C" should be --42°C--.

Col. 6, line 29, "follows" should be --follows:-- (add a space after follows:)

Col. 8, line 62, "wolfeii" should be --*wolfei*--.

Signed and Sealed this

Fourteenth Day of December, 1993

Attest:

BRUCE LEHMAN

Attesting Officer

Commissioner of Patents and Trademarks